United States Patent [19]

Kühle et al.

[11] 3,939,189
[45] Feb. 17, 1976

[54] N-FLUORODICHLOROMETHYLTHIO)-N-(TRIFLUOROMETHYL)-AMINOBENZHYDROXAMIC ACIDS SALTS

[75] Inventors: Engelbert Kühle, Berg. Gladbach; Erich Klauke, Odenthal; Helmut Kaspers; Scheinppflug, both of Leverkusen, all of Germany

[73] Assignee: Bayer Aktiengesellschaft, Leverkusen, Germany

[22] Filed: Feb. 19, 1974

[21] Appl. No.: 443,882

[30] Foreign Application Priority Data
Mar. 10, 1973  Germany............................ 2311983

[52] U.S. Cl. ...................... 260/429.9; 71/3; 71/97; 71/98; 260/429 R; 260/429.9; 260/438.1; 260/439; 260/500; 260/500.5 H; 424/287; 424/289; 424/294; 424/315; 424/335
[51] Int. Cl.² ............................................ C07F 3/06
[58] Field of Search.......... 260/429.9, 429 R, 438.1, 260/439 R

[56] References Cited
UNITED STATES PATENTS
3,843,701  10/1974  Wortham ....................... 260/448 R
3,847,960  11/1974  Avar et al. ...................... 260/439 R FOREIGN PATENTS OR APPLICATIONS
1,543,614  2/1970  Germany
1,210,620  2/1966  Germany
2,223,452  11/1973  Germany OTHER PUBLICATIONS
Chemical Abstracts, V. 65, 13619b (1966).
Chemical Abstracts, V. 66, 94789b (1967).
Chemical Abstracts, V. 66, 99881k (1967).

*Primary Examiner*—Helen M. S. Sneed
*Attorney, Agent, or Firm*—Burgess, Dinklage & Sprung

[57] ABSTRACT

N-(fluorodichloromethylthio)-N-(trifluoromethyl)-aminobenzhydroxamic acids and their salts of the formula

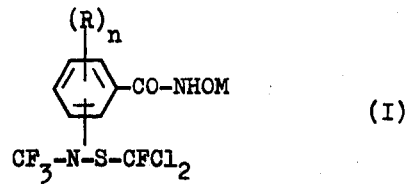

in which
R is halogen, nitro, alkyl or alkoxy with in either case up to 3 carbon atoms, or trifluoromethyl,
n is 0, 1 or 2, and
M is hydrogen or one equivalent of an alkali metal, alkaline earth metal or heavy metal,
which possess fungicidal and microbicidal properties.

4 Claims, No Drawings

N-FLUORODICHLOROMETHYLTHIO)-N-(TRIFLUOROMETHYL)-AMINOBENZHYDROXAMIC ACIDS SALTS

The present invention relates to and has for its objects the provision of particular new N-(fluorodichloromethylthio)-N-(trifluoromethyl)-aminobenzhydroxamic acids and their salts, which possess fungicidal or microbicidal properties, active compositions in the form of mixtures of such compounds with solid and liquid dispersible carrier vehicles, and methods for producing such compounds and for using such compounds in a new way especially for combating pests, e.g. fungi, bacteria and yeasts, with other and further objects becoming apparent from a study of the within specification and accompanying examples.

It has already been disclosed in German Published Specification DOS No. 1,543,614 that N-(trihalogenomethylthio)-N-(trifluoromethyl)-aminobenzamides can be used as fungicides in plant protection. In general, these compounds have a good action; however, the action against some phytopathogenic fungi is not entirely satisfactory if low amounts are used. It is also known from German Published Specification DOS Nos. 1,210,620 and 1,667,975 that aromatic hydroxamic acids and their salts can be employed as seed dressings.

The present invention provides, as new compounds, the N-(fluorodichloromethylthio)-N-(trifluoromethyl)-aminobenzhydroxamic acids and their salts of the general formula

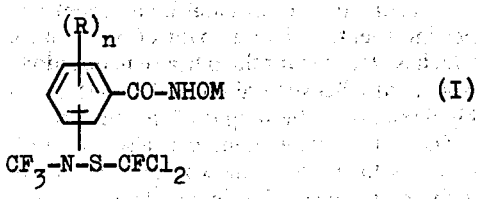

in which
R is halogen, nitro, alkyl or alkoxy with in either case up to 3 carbon atoms, or trifluoromethyl,
$n$ is 0, 1 or 2, and
M is hydrogen or one equivalent of an alkali metal, alkaline earth metal or heavy metal.

The compounds of the formula (I) have been found to possess microbicidal and strong fungicidal properties.

Preferably, R is chlorine, fluorine, nitro, methyl, methoxy or trifluoromethyl, $n$ is 0 or 1, and M is hydrogen or an equivalent of sodium, potassium, magnesium, calcium, zinc, copper, iron, manganese or nickel.

Surprisingly, the compounds according to the invention, of the formula (I), display a very good fungicidal action and surpass known compounds in respect of their activity and toleration by plants. They thus represent an enrichment of the art.

The present invention also provides a process for the preparation of a compound of the general formula (I), in which an N-(fluorodichloromethylthio)-N-(trifluoromethyl)amino-benzoyl chloride of the general formula

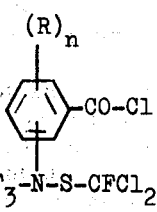

in which
R and $n$ have the above-mentioned meanings,
is reacted with hydroxylamine in the presence of an acidbinding agent, and the hydroxamic acid thereby produced is optionally converted into a salt thereof with an alkali metal hydroxide or alkaline earth metal hydroxide or heavy metal salt.

If 3-[N-(fluorodichloromethylthio)-N-(trifluoromethyl)]aminobenzoyl chloride is used as the starting material, the course of the reaction can be represented by the following equation:

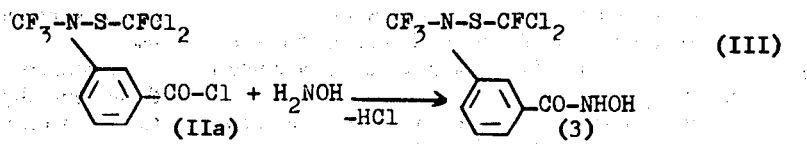

The N-(fluorodichloromethylthio)-N-(trifluoromethyl)-aminobenzoyl chlorides of the formula (II), to be used as starting materials, have not hitherto been described in the literature and can be obtained by reaction of the corresponding benzoic acids with thionyl chloride, preferably in excess, at temperatures in the range of from 20° to 100°C, preferably of from 60° to 80°C. This reaction, and the compounds obtained therefrom, form the subject of Published German Patent Application ("Deutsche Offenlegungsschrift") No. 2,223,452, the disclosure of which is incorporated herein by reference.

Diluents which can be used for the reaction according to the invention are not only water but also lower aliphatic alcohols, such as, for example, methanol and ethanol.

All customary acid-binding agents can be used to bind the acid. These include alkali metal hydroxides, alkaline earth metal hydroxides, alkali metal carbonates and tertiary amines such as, for example, triethylamine. An excess of hydroxylamine can also be used with advantage.

The reaction temperatures can be varied within a fairly wide range. In general, the reaction is carried out at between 0° and 60°C, preferably between 20° and 50°C.

In carrying out the process according to the invention, 1.5 to 5 moles of hydroxylamine are preferably employed per mole of aminobenzoyl chloride derivative. The hydroxylamine may be obtained in the usual manner, for example by reacting a salt thereof such as the hydrochloride, in methanol or ethanol with an alkali metal hydroxide to give the free hydroxylamine. The reaction of the benzoyl chloride with the hydroxylamine is exothermic; after the reaction has subsided, the product is taken up in water and ether and worked up in the usual manner. The crude product is purified by recrystallization, for example from benzene, toluene or xylene.

The salts (I) may be obtained by treating the hydroxamic acid derivatives, in aqueous or aqueous-alcoholic dilution, with an alkali metal hydroxide or alkaline earth metal hydroxide or with a soluble heavy metal salt; an alkali metal carbonate or alkali metal bicarbonate can be used to neutralize the acid which may be liberated.

The active compounds according to the invention display a strong fungitoxic action and are distinguished by a broad spectrum of activity. Their low toxicity towards warmblooded animals and their good toleration by higher plants allows them to be used as plant-protection agents against fungal diseases. They do not harm crop plants in the concentrations necessary for combating the fungi. Fungitoxic agents are employed in plant protection for combating fungi from the most diverse categories of fungi, such as Archimycetes, Phycomycetes, Ascomycetes, Basidiomycetes and *Fungi Imperfecti*.

The active compounds according to the invention can be used against parasitary fungi on above-ground parts of plants, fungi which cause tracheomycosis and which attack the plant through the soil, seed-borne fungi and fungi which inhabit the soil. They are particularly active against fungi of the class of Phycomycetes, for example against *Phytophthora infestans*.

The compounds can also be used as cereal fungicides and as seed dressings. They also possess a good bactericidal activity.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as freon; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides and microbicides, or insecticides, acaricides, rodenticides, nematocides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–2%, preferably 0.0005–0.05%, by weight of the mixture. Thus, the present invention contemplates over-all compositions which comprises mixtures of a conventional dispersible carrier vehicle such as (1) a dispersible inert finely divided carrier solid, and/or (2) a dispersible carrier liquid such as an inert organic solvent and/or water preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.0005–2%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 15 to 1000 g/hectare, preferably 40 to 600 g/hectare, are sufficient. In this process it is possible to use highly concentrated liquid compositions with said liquid carrier vehicles containing from about 20 to about 80 or 95% by weight of the active compound or even the 100% active substance alone, e.g. about 20–100% by weight of the active compound.

Furthermore, the present invention contemplates methods of selectively killing, combating or controlling pests, e.g. fungi and microbes, and more particularly methods of combating at least one of fungi, bacteria and yeast, which comprises applying to at least one of correspondingly (a) such fungi, (b) such bacteria, (c)

such yeast, and (d) the corresponding habitat thereof, i.e. the locus to be protected, a correspondingly combative or toxic amount, i.e. a fungicidally, bactericidally or yeasticidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The synthesis, unexpected superiority and outstanding activity of the particular new compounds of the present invention are illustrated, without limitation, by the following examples:

EXAMPLE 1

Mycelium growth test

Nutrient medium used:
- 20 parts by weight of agar-agar
- 200 parts by weight of potato decoction
- 5 parts by weight of malt
- 15 parts by weight of dextrose
- 5 parts by weight of peptone
- 2 parts by weight of disodium hydrogen phosphate
- 0.3 part by weight of calcium nitrate Proportion of solvent to nutrient medium:
- 2 parts by weight of solvent mixture
- 100 parts by weight of agar nutrient medium Composition of solvent mixture:
- 0.19 part by weight of acetone
- 0.01 part by weight of emulsifier
- 1.80 parts by weight of water
- 2 parts by weight of solvent mixture The amount of active compound required for the desired concentration of active compound in the nutrient medium was mixed with the stated amount of solvent. The concentrate was thoroughly mixed, in the stated proportion, with the liquid nutrient medium (which had been cooled to 42°C) and was then poured into Petri dishes of 9 cm diameter. Control dishes to which the preparation had not been added were also set up.

When the nutrient medium had cooled and solidified, the dishes were inoculated with the species of fungi stated in the table and incubated at about 21°C.

Evaluation was carried out after 4–10 days, dependent upon the speed of growth of the fungi. When evaluation was carried out, the radial growth of the mycelium on the treated nutrient medium was compared with the growth on the control nutrient medium. In the evaluation of the fungus growth, the following characteristic values were used:

- 1 no fungus growth
- up to 3 very strong inhibition of growth
- up to 5 medium inhibition of growth
- up to 7 slight inhibition of growth
- 9 growth equal to that of untreated control.

The active compounds, the concentrations of active compound and the results can be seen from the table which follows:

Table I

| Mycelium growth test Active compounds: | A | B | C | D | E | F | G | H | I | J | K | L | M | N | O | P | Q | R |
|---|---|---|---|---|---|---|---|---|---|---|---|---|---|---|---|---|---|---|
| 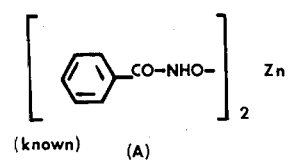 (known) (A) | 10 | 9 | 5 | 9 | 9 | 9 | 5 | 5 | 5 | 5 | 5 | 9 | 3 | 1 | 5 | 5 | 9 | 9 |
|  | 5 | 9 | 9 | 9 | 9 | 9 | 9 | 9 | 9 | 5 | 9 | 9 | 3 | 2 | 5 | 5 | 9 | 9 |
| 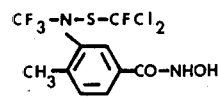 (1) | 10 | 1 | 1 | 2 | 1 | 1 | 1 | 2 | 1 | 5 | 1 | 3 | 1 | 1 | 1 | — | 1 | — |
|  | 5 | 2 | 1 | 3 | 1 | 1 | 1 | 2 | 1 | 9 | 3 | 5 | 1 | 1 | 1 | — | 1 | — |
| 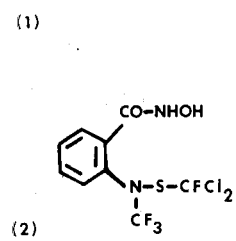 (2) | 10 | 1 | 1 | 2 | 3 | 1 | 1 | 1 | 1 | 3 | 1 | 1 | 1 | 1 | 1 | 1 | 1 | 1 |
|  | 5 | 2 | 2 | 3 | 5 | 1 | 1 | 1 | 1 | 3 | 1 | 1 | 1 | 1 | 1 | 1 | 1 | 9 |

Table I-continued

| Mycelium growth test Active compounds: | | A | B | C | D | E | F | G | H | I | J | K | L | M | N | O | P | Q | R |
|---|---|---|---|---|---|---|---|---|---|---|---|---|---|---|---|---|---|---|---|
| (4) [CF₃–N–S–CFCl₂ / C₆H₄–CO–NHO–]₂ Zn | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>2 |
| (7) [CF₃–N–S–CFCl₂ / C₆H₄–CO–NHO–]₂ Mn | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 |
| (8) [CF₃–N–S–CFCl₂ / C₆H₄–CO–NHO–]₂ Mg | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 2<br>2 |
| (9) [CF₃–N–S–CFCl₂ / C₆H₄–CO–NHO–]₂ Fe | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 |
| (10) [CF₃–N–S–CFCl₂ / C₆H₄–CO–NHO–]₂ Cu | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>5 |
| (11) [CF₃–N–S–CFCl₂ / C₆H₄–CO–NHO–]₂ Ca | 10<br>5 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 | 1<br>1 |
| (5) [CF₃–N–S–CFCl₂ / CH₃–C₆H₃–CO–NHO–]₂ Zn | 10<br>5 | 1<br>1 | 1<br>1 | 1<br>1 | 3<br>3 | 1<br>1 | 1<br>1 | 1<br>1 | 1<br>2 | 1<br>1 | 3<br>5 | 1<br>1 | 1<br>1 | 1<br>1 | 1<br>1 | 1<br>1 | 1<br>1 | 1<br>1 | 1<br>1 |

Table I-continued

| Mycelium growth test Active compounds: | A | B | C | D | E | F | G | H | I | J | K | L | M | N | O | P | Q | R |
|---|---|---|---|---|---|---|---|---|---|---|---|---|---|---|---|---|---|---|
| (6) 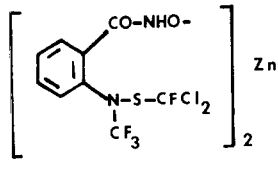 | 10<br>5 | 1<br>3 | 1<br>3 | 3<br>3 | 1<br>9 | 1<br>3 | 1<br>1 | 1<br>3 | 1<br>1 | 3<br>3 | 1<br>1 | 1<br>1 | 1<br>1 | 1<br>1 | 1<br>1 | 1<br>1 | 1<br>1 | 1<br>3 |

A Active compound concentration, ppm
B *Fusarium colmorum*
C *Sclerotinia sclerotiorum*
D *Fusarium nivale*
E *Collectotrichum coffeanum*
F *Rhizoctonia solani*
G *Pythium ultimum*
H *Cochliobolus miyabeanus*
I *Botrytis cinerea*
J *Verticillium alboatrum*
K *Piricularia oryzae*
L *Phialophora cinerescens*
M *Helminthosporium gramineum*
N *Cercospora musae*
O *Phytophthora cactorum*
P *Venturia inaequalis*
Q *Pellicularia sasakii*
R *Xanthomonas oryzae*

EXAMPLE 2

Phytophthora test

| | |
|---|---|
| Solvent: | 4.7 parts by weight acetone |
| Dispersing agent: | 0.3 parts by weight alkylaryl polyglycol ether |
| Water: | 95 parts by weight |

The amount of the active compound required for the desired concentration of the active compound in the spray liquid was mixed with the stated amount of solvent and the concentrate was diluted with the stated amount of water which contained the stated additions.

Young tomato plants (Bonny best) with 2–6 foliage leaves were sprayed with the spray liquid until dripping wet. The plants remained in a greenhouse for 24 hours at 20°C and at a relative atmospheric humidity of 70%. The tomato plants were then inoculated with an aqueous spore suspension of *Phytophthora infestans*. The plants were brought into a moist chamber with an atmospheric humidity of 100% and a temperature of 18°–20°C.

After 5 days the infection of the tomato plants was determined as a percentage of the untreated but likewise inoculated control plants: 0% means no infection; 100% means that the infection was exactly as great as in the case of the control plants.

The active compounds, the concentrations of the active compounds and the results can be seen from the following table:

Table 2

| Phytophthora test Active compound | Infection in % of the infection of the untreated control at an active compound concentration of 0.0062% |
|---|---|
| 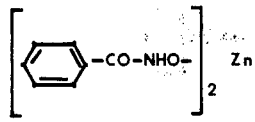<br>(known from German DOS 1,667,975)<br>(B) | 100 |
| 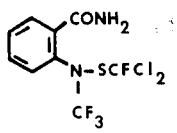<br>(known from German DOS 1,543,614)<br>(C) | 59 |

Table 2-continued
Phytophthora test
| Active compound | Infection in % of the infection of the untreated control at an active compound concentration of 0.0062% |
|---|---|
| 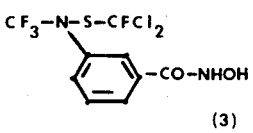 (3) | 5 |
| 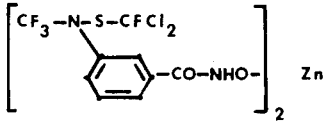 (4) | 11 |
| 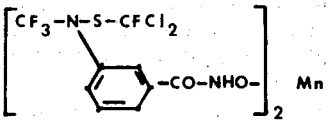 (7) | 10 |
| (8) 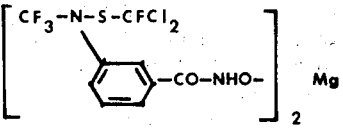 | 16 |
| (9) 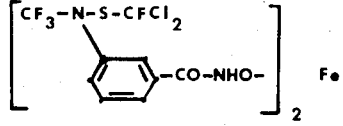 | 22 |
| (10) 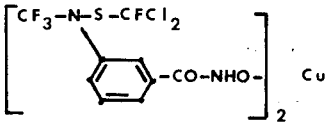 | 10 |
| (11) 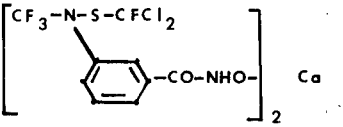 | 27 |

Table 2-continued

Phytophthora test

| Active compound | Infection in % of the infection of the untreated control at an active compound concentration of 0.0062% |
|---|---|
| (5) 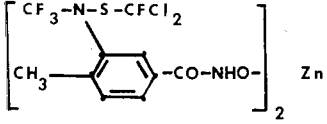 | 29 |
| (6) 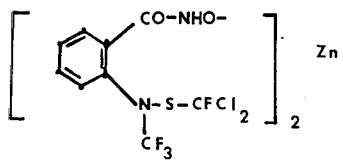 | 25 |

EXAMPLE 3

Botrytis text

Solvent: 4.7 parts by weight of acetone
Dispersing agent: 0.3 part by weight of alkylaryl polyglycol ether
Water: 95 parts by weight The amount of active compound required for the desired concentration of active compound in the spray liquid was mixed with the stated amount of the solvent and the concentrate was diluted with the stated amount of water which contained the stated additives.

Young *Vicia faba* bean plants of the "Zwijndrechter" variety, having 3 to 4 pairs of leaves, were sprayed with the spray liquid until dripping wet.

After 24 hours, the pairs of leaves were removed and the individual leaves were placed in Petri dishes, the lids and bottoms of which were lined with moist filter-paper discs.

Filter-paper discs of 1 cm diameter were dipped into an aqueous spore suspension of *Botrytis cinerea* and placed on the treated leaves lying in Petri dishes. After 48 hours incubation at +20°C the necroses visible under the discs were assessed. 0% denotes no infection and 100% denotes that the infection was exactly as great as in the case of the control plants.

The active compound, active compound concentrations and results can be seen from the table which follows:

Table 3

Botrytis test

| Active compound | Infection in % of the infection of the untreated control at an active compound concentration of | |
|---|---|---|
| | 0.0025% | 0.00062% |
| (known) (A) 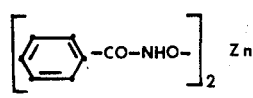 | 16 | 72 |

Table 3-continued

*Botrytis* test

| Active compound | | Infection in % of the infection of the untreated control at an active compound concentration of | |
|---|---|---|---|
| | | 0.0025% | 0.00062% |
| $CF_3$-N-S-$CFCl_2$ on benzene ring with -CO-NHOH | (3) | 0 | 1 |
| $CF_3$-N-S-$CFCl_2$ on benzene ring with -CO-NHOH and 3-methyl | (1) | 0 | |
| benzene ring with -CO-NHOH and N(CF_3)-S-$CFCl_2$ | (2) | 6 | |
| $[CF_3$-N-S-$CFCl_2$ on benzene ring with -CO-NHO-$]_2$ Zn | (4) | 1 | 7 |
| $[CF_3$-N-S-$CFCl_2$ on benzene ring with -CO-NHO-$]_2$ Mn | (7) | 0 | |
| $[CF_3$-N-S-$CFCl_2$ on benzene ring with -CO-NHO-$]_2$ Mg | (8) | 7 | |
| $[CF_3$-N-S-$CFCl_2$ on benzene ring with -CO-NHO-$]_2$ Fe | (9) | 0 | |
| $[CF_3$-N-S-$CFCl_2$ on benzene ring with -CO-NHO-$]_2$ Cu | (10) | 0 | 0 |

Table 3-continued

*Botrytis* test

| Active compound | | Infection in % of the infection of the untreated control at an active compound concentration of | |
|---|---|---|---|
| | | 0.0025% | 0.00062% |
| 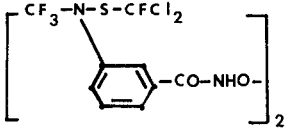 | (11) | 12 | |
| 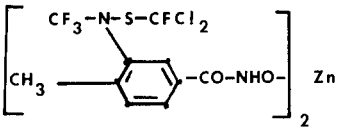 | (5) | 1 | |
| 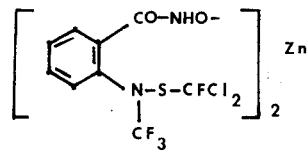 | (6) | 4 | 9 |

EXAMPLE 4

Fusicladium test (apple scab) (Protective)

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated additions.

Young apple seedlings in the 4 – 6 leaf stage were sprayed with the spray liquid until dripping wet. The plants remained in a greenhouse for 24 hours at 20°c and at a relative atmospheric humidity of 70%. They were then inoculated with an aqueous conidium suspension of the apple scab causative organism (*Fusicladium dendriticum* Fuckel) and incubated for 18 hours in a humidity chamber at 18° – 20°C and at a relative atmospheric humidity of 100%.

The plants were then put back into a greenhouse for 14 days.

15 days after inoculation, the infection of the seedlings was determined as a percentage of the untreated but also inoculated control plants. 0% means no infection; 100% means that the infection was exactly as great as in the case of the control plants.

The active compounds, the concentrations of the active compounds and the results can be seen from the following table:

Table 4

*Fusicladium* test/protective

| Active compound | | Infection in % of the infection of the untreated control at an active compound concentration of 0.0025% |
|---|---|---|
| 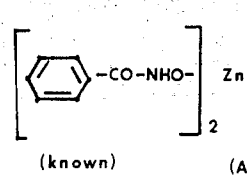 (known) (A) | | 71 |
| 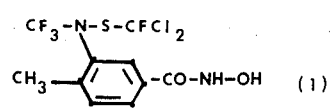 (1) | | 4 |

Table 4-continued

| Active compound (Fusicladium test/protective) | Infection in % of the infection of the untreated control at an active compound concentration of 0.0025% |
|---|---|
| 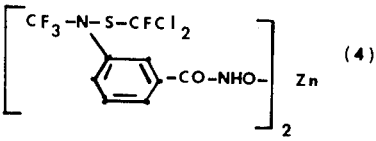 (4) Zn | 15 |
| 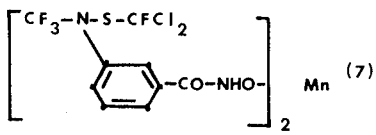 (7) Mn | 6 |
| 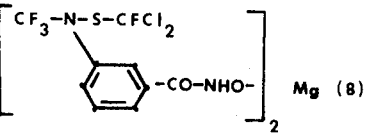 (8) Mg | 10 |
| 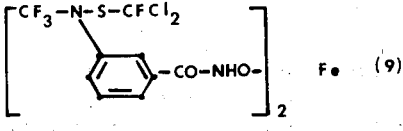 (9) Fe | 9 |

EXAMPLE 5

Microbicidal action/reciprocal minimum inhibition values

The table shows the reciprocal minimum inhibition values for some selected species from the three groups of bacteria, fungi and yeasts. These figures express at what dilutions of the stated compounds the growth of the selected micro-organisms is completely inhibited if these compounds are added to an optimum nutrient for the organisms. The microorganisms employed for this inhibition test are widely encountered and are known to be resistant to conventional chemical preservatives and disinfectants.

The minimum inhibition values listed were determined by the customary dilution method, as follows:

The preparations to be tested were made up at various concentrations in the stated diluent. Certain quantities of the previously dissolved preparations were added to the prepared test tubes filled with standardized nutrient substrates.

All work was carried out under sterile conditions. The various micro-organisms indicated in the table were incubated at 30°C.

The minimum inhibition values shown in the table indicate the concentrations which still suffice to prevent growth.

The diluent was ethylene glycol.

Table 5

| Active compound | Microbicidal action / reciprocal minimum inhibition values | | | | | | | | | |
|---|---|---|---|---|---|---|---|---|---|---|
| | Escherichia coli | Bact. proteus | Bact. mesentericus | Saccharomyces spec. | Pseudomonas aeruginosa | Candida albicans | Trichophyton mentagrophytes | Aspergillus terreus | Aspergillus niger | Penicillium camerunense |
| 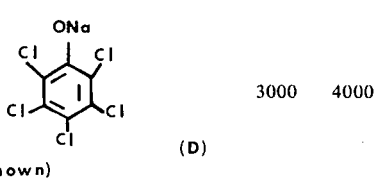 (D) (known) | 3000 | 4000 | | | 3000 | 17000 | | 17000 | | |

Table 5 -continued

| Active compound | Microbicidal action / reciprocal minimum inhibition values | | | | | | | | | |
|---|---|---|---|---|---|---|---|---|---|---|
| | Escherichia coli | Bact. proteus | Bact. mesentericus | Saccharomyces spec. | Pseudomonas aeruginosa | Candida albicans | Trichophyton mentagrophytes | Aspergillus terreus | Aspergillus niger | Penicillium camerunense |
| 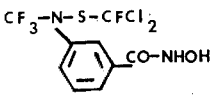 (3) | 13500 | 13500 | 132000 | 132000 | 17000 | 54000 | 135000 | 66000 | 665000 | 27000 |
| 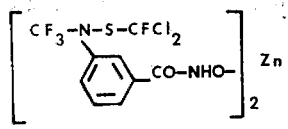 (4) | 12800 | 12800 | 128000 | 128000 | 32000 | 64000 | 128000 | 64000 | 14500 | 14500 |
| 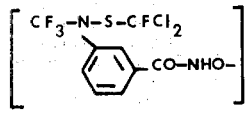 (8) | 6900 | 6900 | 138000 | 64000 | 34500 | 69000 | 64000 | 69000 | 32000 | 64000 |
| 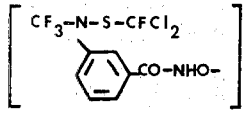 (7) | 16000 | 16000 | 69000 | 69000 | 34500 | 69000 | 138000 | 138000 | 138000 | 138000 |
| 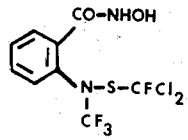 (2) | 14400 | 14400 | 72000 | 72000 | 15000 | 30000 | 144000 | 72000 | 72000 | 72000 |

The process of the present invention is illustrated by the following preparative Examples.

EXAMPLE 6

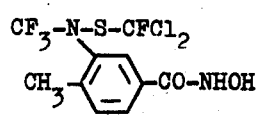 (1)

37 g (0.1 mole) of 3-[N-(fluorodichloromethylthio)-N-(trifluoromethyl)-amino]-4-methyl-benzoyl chloride were added dropwise at room temperature, while stirring, to a hydroxylamine solution (about 0.25 mole) prepared from 18 g of hydroxylamine hydrochloride and 15 g of potassium hydroxide in 100 ml of methanol, and the temperature was allowed to rise to about 30°C. After the reaction had subsided, the solution was taken up in ether and extracted by shaking with water, and the ether solution was concentrated in vacuo. 34 g of a solid residue were obtained. Crystallization from xylene with the addition of a little petroleum ether gave 25 g of 3-[N-(fluorodichloromethylthio)-N-(trifluoromethyl)-amino]-4-methylbenzhydroxamic acid of melting point 157° – 158°C (with decomposition). The yield was 72% of theory.

The benzoyl chloride derivative required as an intermediate was obtained by reaction of 0.5 mole of 3-[N-(fluorodichloromethylthio)-N-(trifluoromethyl)-amino]-4-methylbenzoic acid with 400 ml of thionyl chloride at 45° – 50°C. As soon as the evolution of hydrogen chloride subsided, the reaction temperature was raised to the boil, the solution was then concentrated and the residue was distilled. The boiling point of the product was 95°C/0.05 mm Hg.

The aminobenzoic acid derivatives to be used as starting materials are known (see British Patent Specification No. 1,229,083); they are obtained by the action of formic acid on N-sulfenylated N-trifluoromethyl-aminobenzoic acid fluorides at, preferably 80° – 110°C, it being possible to use excess formic acid as the solvent.

The following compounds could be prepared by methods similar to that described in Example 6.

EXAMPLE 7

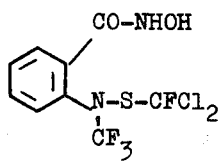 (2)

Melting point 148° – 149°C (with decomposition).

EXAMPLE 8

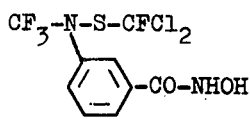 (3)

Melting point 107° – 109°C.

EXAMPLE 9

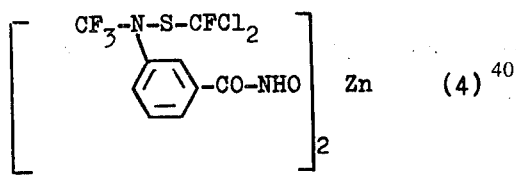 (4)

7 g of 3-[N-(fluorodichloromethylthio)-N-(trifluoromethyl)-amino]-benzhydroxamic acid were dissolved in 125 ml of methanol and a solution of 2 g of sodium bicarbonate in 30 ml of water, followed by a solution of 3 g of zinc sulfate (ZnSO$_4$ . 7 H$_2$O) in 20 ml of water, were added. On adding further water, the above zinc salt precipitated.

Melting point 170° – 180°C (with decomposition). The yield was 7 g.

The following salts were obtained similarly:

EXAMPLE 10

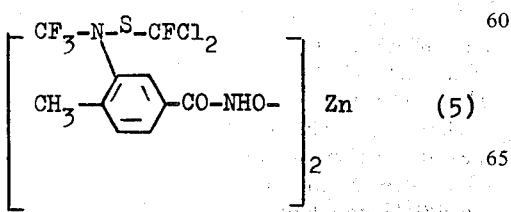 (5)

Melting point 175°C (with decomposition).

EXAMPLE 11

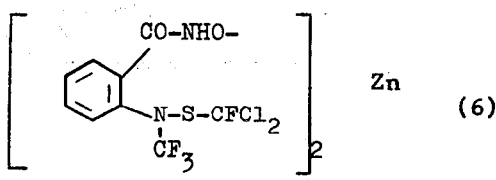 (6)

Melting point 140° – 145°C (with decomposition)

The following salts of the general formula

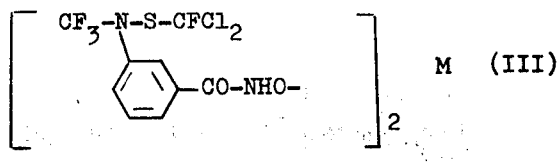 (III)

could also be obtained by methods analogous to that of

Example 9

| Compound No. | M | Melting point, °C |
|---|---|---|
| 7 | Mn(II) | 160 (with decomposition) |
| 8 | Mg | 170 (with decomposition) |
| 9 | Fe(II) | 170–175 (with decomposition) |
| 10 | Cu(II) | 180–185 (with decomposition) |
| 11 | Ca | 110–120 (with decomposition) |

Other compounds which can be similarly prepared include:
sodium 4-[N-(fluorodichloromethylthio)-N-(trifluoromethyl)-amino]-2-trifluoromethylbenzhydroxamate,
potassium 2-[N-(fluorodichloromethylthio)-N-(trifluoromethyl)-amino]-4-isopropyl-6-methoxy-benzhydroxamate,
nickel 3-[N-(fluorodichloromethylthio)-N-(trifluoromethyl)-amino]-4-fluoro-5-chloro-benzhydroxamate,
barium 3-[N-(fluorodichloromethylthio)-N-(trifluoromethyl)-amino]-4-nitro-benzhydroxamate,
and the like.

It will be appreciated that the instant specification and examples are set forth by way of illustration and not limitation, and that various modifications and changes may be made without departing from the spirit and scope of the present invention.

What is claimed is:

1. An N-(fluorodichloromethylthio)-N-(trifluoromethyl)-amino-benzhydroxamic acid or salt of the formula

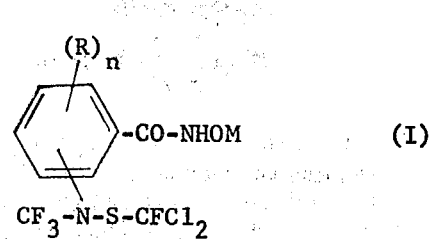 (I)

in which
R is halogen, nitro, alkyl or alkoxy with in either case up to 3 carbon atoms, or trifluoromethyl,
n is 0, 1 or 2, and
M is (hydrogen or one) an equivalent of (an alkali metal, alkaline earth metal or heavy metal) zinc, copper, iron, manganese or nickel.

2. The compound according to claim 1 wherein such compound is zinc 3-[N-(fluorodichloromethylthio)-N-(trifluoromethyl)-amino]-benzhydroxamate of the formula

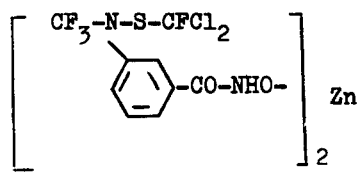

3. The compound according to claim 1 wherein such compound is zinc 2-[N-fluorodichloromethylthio)-N-(trifluoromethyl)-amino]-benzhydroxamate of the formula

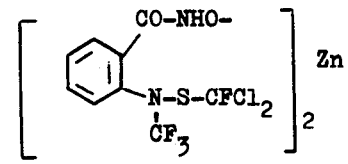

4. The compound according to claim 1 wherein such compound is manganese 3-[N-(fluorodichloromethylthio)-N-(trifluoromethyl)-amino]-benzhydroxamate of the formula

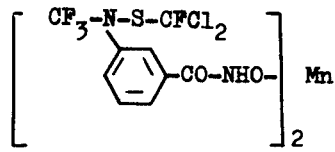

* * * * *

UNITED STATES PATENT AND TRADEMARK OFFICE
CERTIFICATE OF CORRECTION

PATENT NO. : 3,939,189
DATED : February 17, 1976
INVENTOR(S) : Engelbert Kuhle et al It is certified that error appears in the above-identified patent and that said Letters Patent are hereby corrected as shown below:

Claim 1

| | |
|---|---|
| Col. 24, line 56 | delete "or" |
| Col. 25, line 5 | delete "(hydrogen or one)" |
| Col. 25, lines 5-6 | delete "(an alkali metal, alkaline earth metal or heavy metal)" |

Signed and Sealed this thirtieth Day of August 1977

[SEAL]

Attest:

RUTH C. MASON
*Attesting Officer*

C. MARSHALL DANN
*Commissioner of Patents and Trademarks*